(12) United States Patent
Castaneda

(10) Patent No.: US 9,983,043 B2
(45) Date of Patent: May 29, 2018

(54) POSITIONING APPARATUS FOR A LIQUID LEVEL SENSOR

(71) Applicant: Heateflex Corporation, Arcadia, CA (US)

(72) Inventor: Hector Joel Castaneda, Cypress, CA (US)

(73) Assignee: Heateflex Corporation, Arcadia, CA (US)

( * ) Notice: Subject to any disclaimer, the term of this patent is extended or adjusted under 35 U.S.C. 154(b) by 157 days.

(21) Appl. No.: 14/957,863

(22) Filed: Dec. 3, 2015

(65) Prior Publication Data

US 2017/0160122 A1    Jun. 8, 2017

(51) Int. Cl.
*G01F 23/26* (2006.01)
*G01D 11/30* (2006.01)
*G01N 29/22* (2006.01)

(52) U.S. Cl.
CPC .......... *G01F 23/268* (2013.01); *G01D 11/30* (2013.01); *G01F 23/263* (2013.01); *G01N 29/223* (2013.01)

(58) Field of Classification Search
CPC .... G01F 23/268; G01D 11/30; G01N 29/223; G01K 1/143

USPC ........................................................ 73/866.5
See application file for complete search history.

(56) References Cited

U.S. PATENT DOCUMENTS

| | | | | |
|---|---|---|---|---|
| 5,858,311 A | * | 1/1999 | Bachtel | C10G 49/26 122/511 |
| 2008/0053255 A1 | * | 3/2008 | Furey | G01D 11/245 73/866.5 |
| 2008/0163692 A1 | * | 7/2008 | Huang | G01F 1/663 73/627 |
| 2013/0213130 A1 | * | 8/2013 | Ohmiya | G01F 1/34 73/201 |

* cited by examiner

*Primary Examiner* — Daniel S Larkin
*Assistant Examiner* — Nathaniel Kolb
(74) *Attorney, Agent, or Firm* — Kelly & Kelley, LLP

(57) ABSTRACT

A positioning apparatus for a liquid level sensor includes a liquid level sensor support, such as a generally horizontal platform, having an aperture for receiving at least a portion of the liquid level sensor. An arm extends from the support and has an aperture for receiving a liquid outlet tube extending from an outlet of a liquid pass-through device. A hollow socket is spaced apart from the arm and removably attachable to the outlet of the liquid pass-through device. The apparatus maintains the relative position and orientation of the liquid level sensor to the liquid outlet tube extending from the outlet of the liquid pass-through device.

17 Claims, 4 Drawing Sheets

POSITIONING APPARATUS FOR A LIQUID LEVEL SENSOR

BACKGROUND OF THE INVENTION

The present invention generally relates to brackets for holding liquid level sensors. More particularly, the present invention is directed to an apparatus for maintaining a liquid level sensor relative to a liquid outlet tube extending from an outlet of a liquid pass-through device.

Certain liquid pass-through devices, such as in-line fluid heaters and pumps, will be damaged if powered on without fluids. For example, the heating element in an in-line heater designed for heating liquids will typically burn out if operated in a dry condition as the heating element will not be able to dissipate the heat generated without the presence of liquid, thereby damaging the heating element. In a pump, operating in a dry condition can damage the internal mechanical parts by excessive friction or heat.

Therefore, it is common practice to install a liquid level sensor on the output side of such devices and interlock the sensor to the device's power in a manner in which the device can only be powered on when liquid is present. The liquid sensor is placed on the output side of the device to provide a means to electronically indicate when the liquid has flowed through the device, and therefore is safe to operate and power on. One liquid level sensor type commonly used for this application is a capacitive liquid level sensor. These sensors are desirable as they function outside the fluid path and therefore do not come in direct wetted contact with the process fluid, which is particularly desirable when the purity of the process fluid is important.

As the sensor reacts to the presence of liquid present in the tubing, a bracket is required to hold the sensor in place for proper operation. An unreliable sensor reading can result from improperly installing the sensor too close to the tubing or by changing the distance between the sensor and the tubing after calibration. Unreliable sensor readings can also result if the tubing sags, resulting in a change of distance between the tubing and the sensor. Moving the sensor farther upstream from the device could also result in faulty readings since a user can mistakenly place the sensor in a portion of the liquid path (tubing) that contains liquid in all conditions even though the liquid pass-through device does not contain liquid. This can happen, for example, in a section of piping similar to a P-trap or the like.

Therefore, there is a continuing need for an apparatus that will hold a liquid level sensor in such a manner so as to keep the distance between the sensor and the tubing fixed. Such an apparatus should not allow the tubing to sag in the section that the sensor is located. Moreover, such an apparatus should not allow a user to move the sensor to a different location of the tubing. The present invention fulfills these needs, and provides other related advantages.

SUMMARY OF THE INVENTION

The present invention resides in a positioning apparatus for maintaining a liquid level sensor relative to a liquid outlet tube extending from an outlet of a liquid pass-through device, such as an in-line liquid heater or a liquid pump.

The apparatus generally comprises a liquid level sensor support. The liquid level sensor support may comprise a generally horizontal platform having an aperture for receiving at least a portion of the liquid level sensor. An arm extends from the support and has an aperture for receiving the liquid outlet tube. A second arm extends from the support in spaced relation to the first arm and has a liquid outlet tube receiving aperture aligned with the liquid outlet tube receiving aperture of the first arm.

A hollow socket is attached to or extends from the second arm and is removably attachable to an outlet of the liquid pass-through device. A screw or bolt may be insertable into an aperture formed in a side wall of the socket to fasten the socket to the liquid pass-through device outlet. An inner surface of the socket may have a mating configuration to an outer surface of the liquid pass-through device outlet so as to be slidingly attachable thereto while preventing rotation of the socket relative to the outlet. Thus, the relative position and orientation of the liquid level sensor to the liquid outlet tube is maintained.

Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENTS

Figure 1:
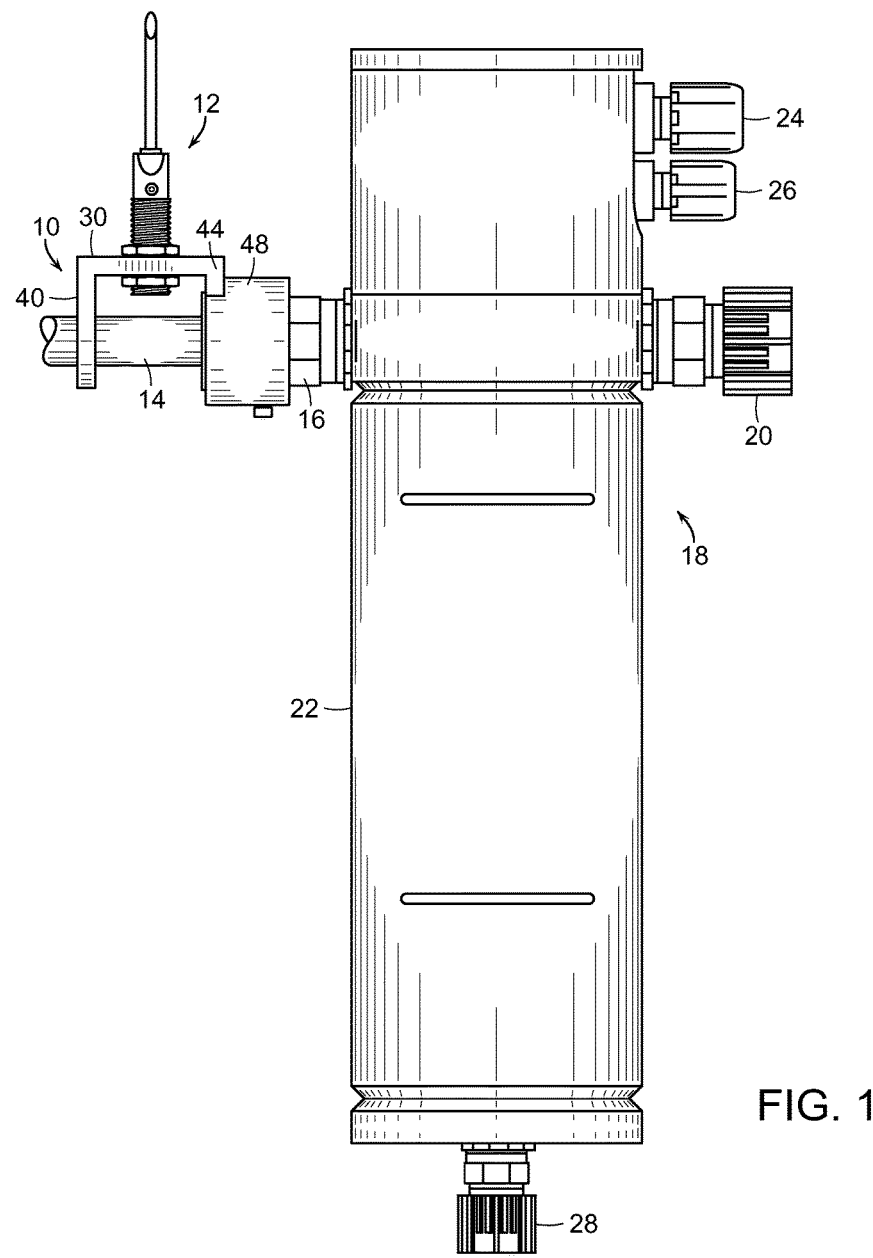
FIG. 1 is a side elevational view of a liquid pass-through device in the form of an in-line heater having the apparatus of the present invention attached thereto.

As shown in the accompanying drawings, for purposes of illustration, the present invention resides in an apparatus, generally referred to by the reference number 10, that positions and maintains a liquid level sensor 12 relative to a liquid outlet tube 14 extending from an outlet 16 of a liquid pass-through device 18. The apparatus 10 of the present invention is configured and designed to keep the liquid level sensor 12 at a fixed distance relative to the outlet tubing 14, does not allow the tubing 14 to sag relative to the sensor, and does not allow a user to move the sensor 12 to a different location on the liquid outlet tubing 14.

With reference now to FIG. 1, the apparatus 10 of the present invention is shown with a liquid level sensor 12 attached thereto. A number of different liquid level sensors 12 may be used in accordance with the present invention, but the present invention is particularly suited for use with capacitive liquid level sensors. Such sensors are desirable in applications where it is preferred that the sensor does not come into direct contact with the process fluid, such as due to process fluid purity concerns or the caustic nature of process fluid. As the capacitive liquid level sensor functions outside the fluid path, and does not come in direct wetted contact with the process fluid, it is particularly useful in such applications.

As is known in the art, a capacitive liquid level sensor is installed a desired distance from the liquid tubing 14 and calibrated so as to provide reliable sensor readings of the liquid passing through the tube 14. Accordingly, maintaining the relative position and distance and orientation to the tubing 14 is important in order to keep reliable sensor readings. As will be more fully described herein, the present invention is designed and configured to properly position and maintain the liquid level sensor 12 relative to the liquid outlet tube 14, as well as the liquid pass-through device 18, to meet these desired requirements.

With continuing reference to FIG. 1, the apparatus 10 of the present invention is removably attached to an outlet 16 of the liquid pass-through device 18. The liquid outlet tube 14 extends from the outlet 16 through the apparatus 10 and typically in spaced relation to the liquid level sensor 12.

The liquid pass-through device 18 can comprise a variety of devices in which it is important that liquid be present within the device 18 in order to properly operate without being damaged. An in-line liquid heater is illustrated in FIG. 1 for exemplary purposes. As mentioned above, it is important that liquid be present and passing through the in-line heater device 18 before the heater is powered and its heating elements heated in order to avoid damaging the heating elements and the heater device 18. In the heater device 18 illustrated in FIG. 1, a liquid inlet 20 supplies a source of liquid into the container or housing 22, which then passes through the outlet 16 of the device 18. Lead wires and the like (not shown) may pass through fittings 24 and 26 so as to provide electrical power necessary to the heating elements within the heater device 18 and the like. The heater device 18 may also include a liquid discharge port 28, as illustrated in FIG. 1. However, it will be appreciated that other configurations and designs of in-line heater devices may be used, or even other liquid pass-through devices such as a liquid pump or the like.

Figure 2:
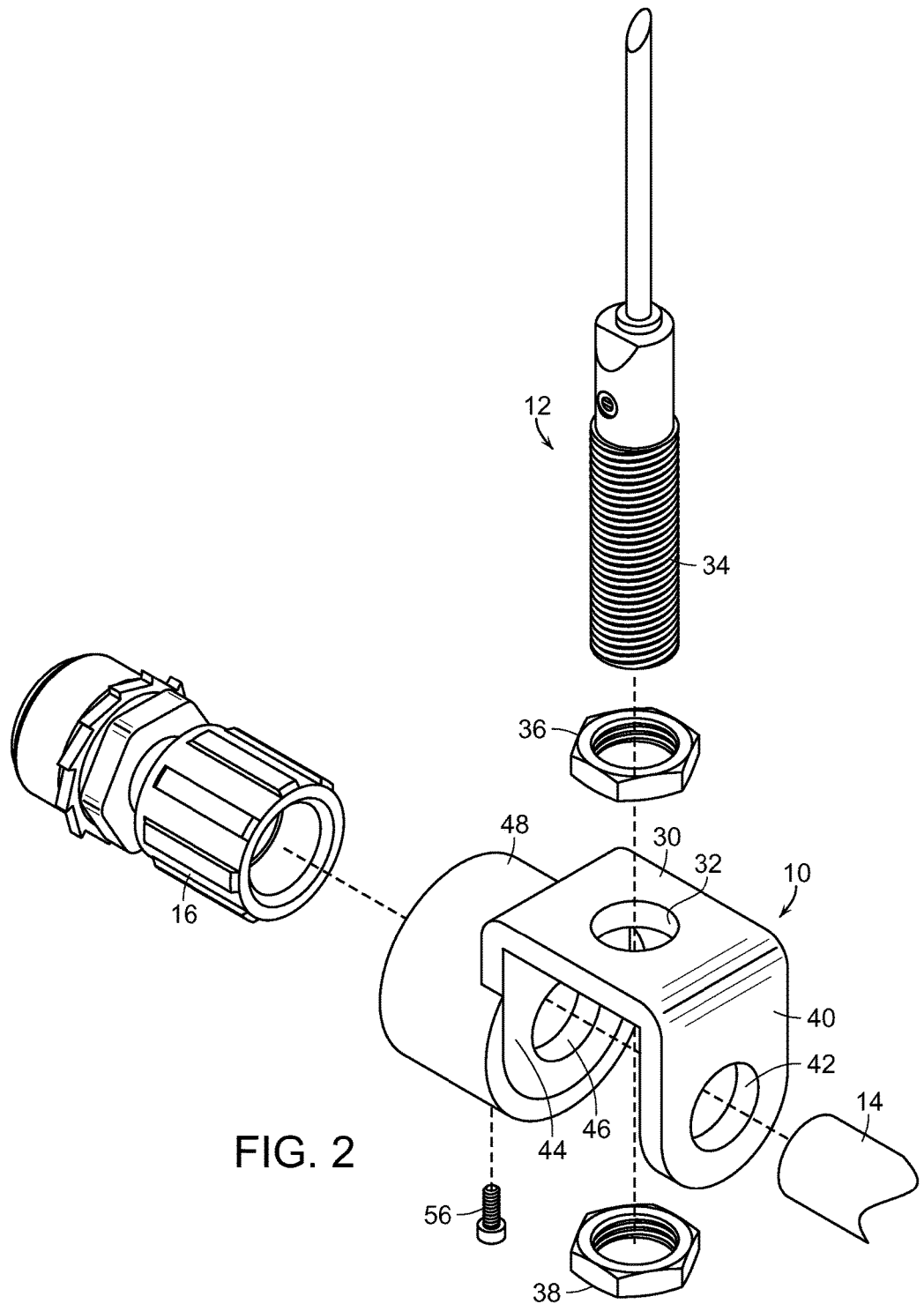
FIG. 2 is an exploded perspective view of the apparatus of the present invention and a liquid level sensor and an outlet of a liquid pass-through device.

With reference now to FIG. 2, the apparatus 10 of the present invention comprises a liquid level sensor support 30, typically in the form of a generally horizontal platform, having an aperture 32 for receiving a portion of the liquid level sensor 12 therethrough. In the illustrated embodiment, a lower portion of the liquid level sensor 12 has threads 34. A first threaded nut 36 is threadedly attached to the liquid level sensor 12. The portion of the liquid level sensor 12 disposed below the first attached nut 36 extends through the aperture 32 of the sensor support 30 of the apparatus 10. A second threaded nut 38 is then threadedly attached to the portion of the liquid level sensor 12 extending below the liquid level sensor support platform 30 and tightened so as to hold the liquid level sensor 12 in place. It will be appreciated that the liquid level sensor 12 can be raised and lowered by the loosening and tightening of the nuts 36 and 38 so as to position the liquid level sensor 12 relative to the liquid tubing 14 and calibrate the liquid level sensor 12.

A first arm 40 extends from the support platform 30. The arm 40 includes an aperture 42 for receiving the liquid outlet tube 14 therethrough. A second arm 44 extends from the support platform 30 in spaced relation to the first arm 40. The second arm 44 includes an aperture 46 which is aligned with the aperture 42 of the first arm 40 and also sized and configured so as to receive the liquid outlet tube 14 therethrough. Typically, the arms 40 and 44 extend from the support platform 30 at similar angles, typically approximately a ninety degree angle, so as to extend generally perpendicular and downward with respect to the support platform 30. The arms 40 and 44 are spaced apart from one another a sufficient distance so that a length of the liquid outlet tubing 14 can extend therebetween and the liquid level sensor 12 obtain readings therefrom, but a sufficiently close distance that the liquid outlet tube 14 will not sag, which could undesirably alter the readings of the sensor 12.

In order to force an installer to attach the apparatus 10 of the present invention to the output connector or outlet 16 of the liquid pass-through device 18, and not further upstream away from the device 18, the apparatus 10 includes a socket 48 which is configured to be removably attachable to the outlet 16 of the liquid pass-through device 18. The socket 48 is typically generally cylindrical in configuration and hollow and having an interior diameter which is slightly greater than the outer diameter of the outlet connector 16 of the liquid pass-through device 18, so as to be slid thereover and attached thereto. The hollow nature of the socket 48 enables the liquid outlet tube 14 to extend from the outlet connector 16 of the liquid pass-through device 18, through the socket 48, and then through apertures 46 and 42 of the second and first arms 44 and 40, respectively.

The socket 48 extends from the second arm 44. The socket 48 may be attached to the second arm 44, such as by adhesive, welding or the like. It will also be appreciated that the socket 48 and second arm 44 could be formed as a single member. In fact, the present invention contemplates that the entire apparatus 10 could be formed as a unitary piece which can be molded, milled or the like to form the component parts or segments thereof. Alternatively, the components can be attached to one another.

Figure 3:
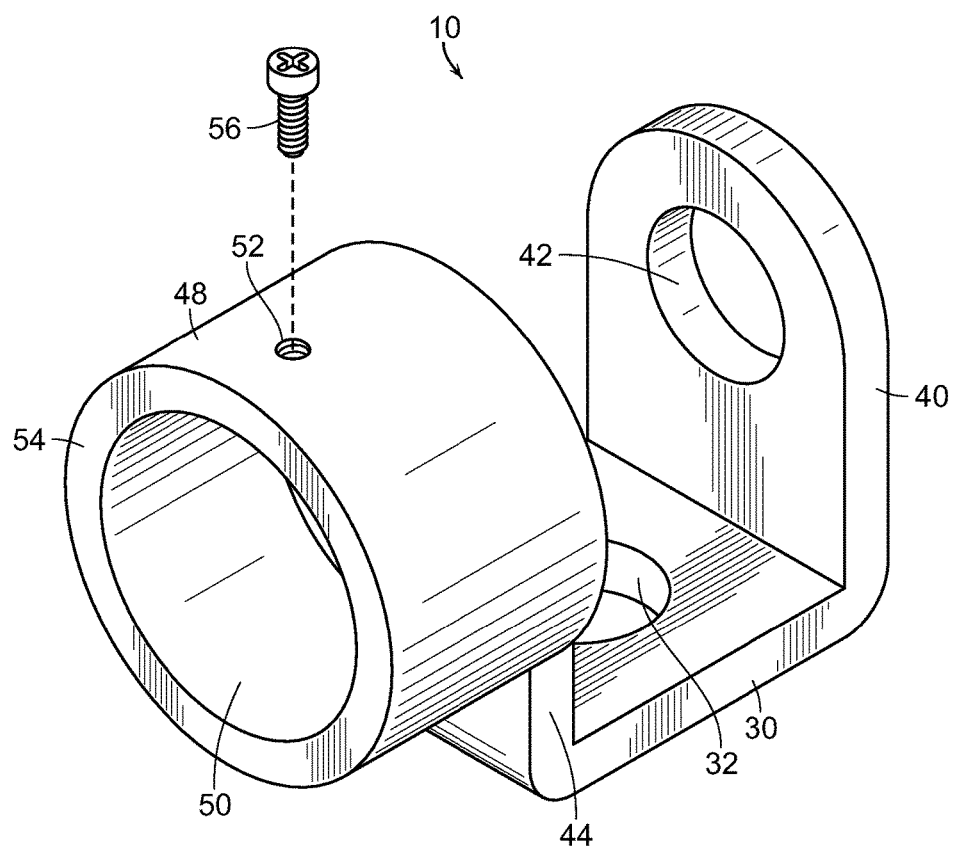
FIG. 3 is a perspective view of the apparatus of the present invention having a fastening screw exploded therefrom.

With reference now to FIG. 3, the inner surface 50 of the socket 48 may be smooth, and define an inner diameter which is slightly greater than the outer diameter of the outlet connector 16 so as to be slidingly, yet preferably frictionally, fit thereon. To ensure a connection, an aperture 52 is formed through the side wall 54 and a screw or bolt 56 inserted therein and into contact with the outlet connector 16 so as to hold the apparatus 10 firmly in place with respect to the outlet connector 16.

Figure 4:
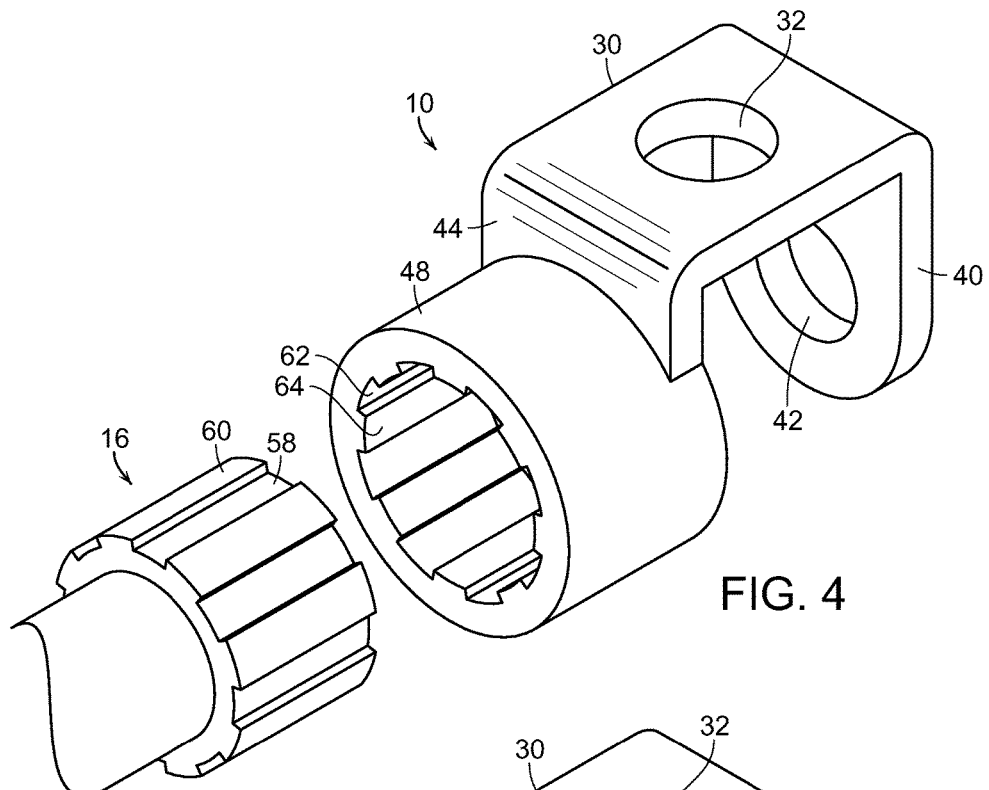
FIG. 4 is a perspective view illustrating an inner surface of a socket of the apparatus of the present invention having a mirror configuration to the outlet of the liquid pass-through device and exploded therefrom.
Figure 5:
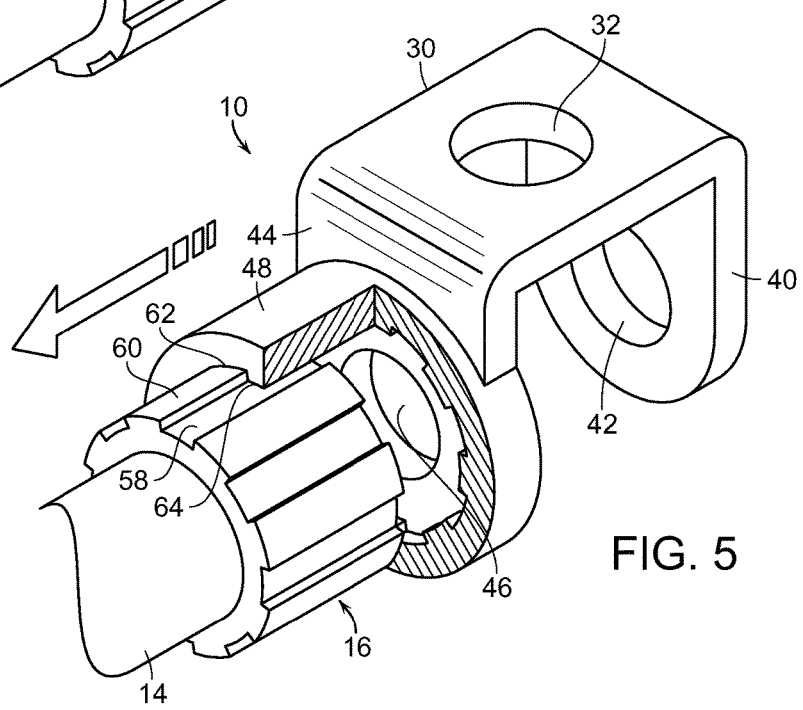
FIG. 5 is a perspective and partially sectioned view illustrating the apparatus of the present invention being slidably attached to the outlet of the liquid pass-through device, in accordance with the present invention.

With reference to FIGS. 4 and 5, the inner surface of the socket 48 may also be configured so as to have a mirror or mating configuration to an outer surface of the liquid pass-through device outlet connector 16 so as to be slidingly attachable thereto, while preventing rotation of the socket 48, and thus apparatus 10, relative to the outlet fitting 16. For example, as illustrated in FIGS. 4 and 5, the outlet fitting 16 includes a series of grooves which are spaced apart from one another, forming elevated sections 60. Grooves 62 are formed on the inner surface of the socket 48 which are sized and configured so as to receive the elevated sections 60, as illustrated in FIGS. 4 and 5 as the apparatus 10 of the present invention is moved and slid into connection with the outlet connector 16. The resulting extensions or tongues 64 of the inner surface of the socket 48 are inserted within the grooves 58 of the outlet connector 16, as illustrated in FIG. 5. This forms a sliding, frictional fit between the outlet connector 16 and the apparatus 10 of the present invention. Moreover, it will prevent the apparatus 10, and liquid level sensor 12, from rotating with respect to the outlet connector 16.

It will be understood that the apparatus 10 is typically disposed with respect to the outlet connector 16 as shown in FIG. 1 so that the liquid level sensor 12 is upright. However, the liquid level sensor 12 could be positioned at any desired angle, so long as it is positioned as desired and maintained in such position with respect to the liquid pass-through device 18 and more particularly the liquid outlet tube 14. It will also be appreciated that the outer configuration of the outlet connector 16 and the corresponding mating inner surface configuration could vary from that illustrated in FIGS. 4 and 5, yet still achieve the objectives of the present invention of removably attaching the apparatus 10 to the outlet connector 16 and maintaining the position of a liquid level sensor 12 with respect to the liquid pass-through device 18 and liquid outlet tube 14. An aperture through the side wall and corresponding screw or bolt could also be incorporated into the embodiment illustrated in FIGS. 4 and 5 so as to securely hold the apparatus 10 to the outlet connector 16.

It will be appreciated by those skilled in the art that the incorporation of the socket 48 into the apparatus 10 forces one to install the apparatus 10 of the present invention onto the outlet connector 16 of the liquid pass-through device 18 and not farther upstream from the liquid pass-through device 18. If the apparatus 10 of the present invention is positioned along the liquid outlet tube 14 at a distance from the liquid pass-through device 18, the apparatus 10 and the liquid level sensor 12 will not remain upright as it would freely rotate around the liquid tubing 14. Forcing the user to attach the socket 48 to the outlet connector or fitting 16 of the liquid pass-through device 18 will maintain the proper and desired position and orientation of the liquid level sensor 12 to the liquid outlet tube 14. Moreover, it will position the liquid level sensor 12 adjacent to the liquid outlet tube 14 where the liquid tube 14 immediately attaches to the liquid pass-through device 18, ensuring correct readings as to whether liquid is present and/or passing through the tube 14, and thus the liquid pass-through device 18.

Although several embodiments have been described in detail for purposes of illustration, various modifications may be made without departing from the scope and spirit of the invention. Accordingly, the invention is not to be limited, except as by the appended claims.

What is claimed is:

1. An apparatus for maintaining a liquid level sensor relative to a liquid outlet tube extending from an outlet of a liquid pass-through device, comprising:
   a liquid level sensor support;
   an arm extending from the support and having an aperture for receiving the liquid outlet tube therethrough; and
   a hollow socket spaced apart from the arm and removably attachable to an exterior portion of an outlet of the liquid pass-through device and having a passageway generally aligned with the arm aperture for receiving the liquid outlet tube therethrough, such that the apparatus has a liquid contact-free attachment to the liquid pass-through device;
   wherein the relative position and orientation of the liquid level sensor to the liquid outlet tube is maintained;
   wherein the liquid level sensor support comprises a generally horizontal platform having an aperture for receiving at least a portion of the liquid level sensor; and
   wherein an inner surface of the socket has a mating configuration to an outer surface of the liquid pass-through device outlet.

2. The apparatus of claim 1, wherein the mating configuration includes a screw or bolt insertable into an aperture formed in a side wall of the socket to fasten the socket to the liquid pass-through device outlet.

3. The apparatus of claim 1, the mating configuration of the inner surface to the outer surface is slidingly attachable thereto while preventing rotation of the socket relative to the outlet.

4. The apparatus of claim 1, including a second arm extending from the liquid level sensor support, the second arm having a liquid outlet tube receiving aperture.

5. The apparatus of claim 4, wherein the liquid outlet tube receiving apertures of the first and second arms are aligned with one another.

6. The apparatus of claim 1, wherein the liquid pass-through device comprises an in-line liquid heater or a liquid pump.

7. The apparatus of claim 1, wherein the first arm extends from the liquid level sensor support at a non-parallel angle relative to the horizontal platform.

8. The apparatus of claim 7, wherein the first arm is generally perpendicular to the horizontal platform.

9. The apparatus of claim 2, wherein the aperture of the horizontal support platform is aligned with the liquid outlet tube extending between the first arm aperture and the passageway of the hollow socket.

10. An apparatus for maintaining a liquid level sensor relative to a liquid outlet tube extending from an outlet of a liquid pass-through device, comprising:
    a liquid level sensor support comprising a generally horizontal platform having an aperture for receiving at least a portion of the liquid level sensor;
    a first arm extending from the support at a non-parallel angle relative to the platform and having an aperture for receiving the liquid outlet tube therethrough;
    a second arm extending from the support in spaced relation to the first arm and having a liquid outlet tube receiving aperture for receiving the liquid outlet tube therethrough, the liquid outlet tube of the second arm being generally aligned with the liquid outlet tube receiving aperture of the first arm;
    a hollow socket extending from the second arm and removably attachable to an exterior portion of an outlet of the liquid pass-through device; and
    a screw or bolt insertable into an aperture formed in a side wall of the socket to fasten the socket to the outlet of the liquid pass-through device;
    wherein the relative position and orientation of the liquid level sensor to the liquid outlet tube is maintained; and
    wherein the apparatus has a liquid contact-free attachment to the liquid pass-through device.

11. The apparatus of claim 10, wherein the liquid pass-through device comprises an in-line liquid heater or a liquid pump.

12. The apparatus of claim 10, wherein the first and second arms are generally perpendicular to the horizontal platform.

13. The apparatus of claim 10, wherein the aperture of the horizontal support platform is generally aligned with the liquid outlet tube extending between the apertures of the first and second arms.

14. An apparatus for maintaining a liquid level sensor relative to a liquid outlet tube extending from an outlet of a liquid pass-through device, comprising:
    a liquid level sensor support comprising a generally horizontal platform having an aperture for receiving at least a portion of the liquid level sensor;
    a first arm extending from the support at a non-parallel angle relative to the platform and having an aperture for receiving the liquid outlet tube therethrough;
    a second arm extending from the support in spaced relation to the first arm and having a liquid outlet tube receiving aperture for receiving the liquid outlet tube therethrough, the liquid outlet tube of the second arm being generally aligned with the liquid outlet tube receiving aperture of the first arm; and a hollow socket extending from the second arm and removably attachable to an exterior portion of an outlet of the liquid pass-through device;

wherein an inner surface of the socket has a mating configuration to an outer surface of the liquid pass-through device outlet so as to be slidingly attachable thereto while preventing rotation of the socket relative to the outlet; and wherein the relative position and orientation of the liquid level sensor to the liquid outlet tube is maintained; and wherein the apparatus has a liquid contact-free attachment to the liquid pass-through device.

15. The apparatus of claim 14, wherein the liquid pass-through device comprises an in-line liquid heater or a liquid pump.

16. The apparatus of claim 14, wherein the first and second arms are generally perpendicular to the horizontal platform.

17. The apparatus of claim 14, wherein the aperture of the horizontal support platform is generally aligned with the liquid outlet tube extending between the apertures of the first and second arms.

* * * * *